United States Patent [19]

Zardi

[11] Patent Number: 4,613,696
[45] Date of Patent: Sep. 23, 1986

[54] PROCESS FOR UREA PRODUCTION

[75] Inventor: Umberto Zardi, Via Lucino 57, Breganzona, Switzerland

[73] Assignees: Umberto Zardi; Ammonia Casale S.A., both of Switzerland

[21] Appl. No.: 729,528

[22] Filed: May 2, 1985

[30] Foreign Application Priority Data

May 19, 1984 [CH] Switzerland ............... 2477/84

[51] Int. Cl.$^4$ ............... C07C 126/02; C07C 126/08
[52] U.S. Cl. ............... 564/67; 564/72; 564/73
[58] Field of Search ............... 564/67, 73, 72

[56] References Cited

U.S. PATENT DOCUMENTS 4,235,816 12/1980 Lagana et al. ............... 564/72
4,301,299 12/1981 Inoue et al. ............... 564/72
4,311,856 1/1982 Inoue et al. ............... 564/67

FOREIGN PATENT DOCUMENTS 98396 1/1984 European Pat. Off. ............... 564/73

Primary Examiner—Charles F. Warren
Assistant Examiner—R. A. Picàrd
Attorney, Agent, or Firm—Ostrolenk, Faber, Gerb & Soffen

[57] ABSTRACT

A process for the production of urea from ammonia and carbon dioxide via synthesis where the urea formation takes place in a synthesis zone (or zones) in which an excess of free ammonia is kept to favor high conversions, said synthesis zone (or zones) being followed by an ammonia separation and direct recycle to the reaction step, where the urea solution from said reaction zone (or zones) is intimately contacted for a short duration time with a minor portion of the fresh $CO_2$. The separation step is followed by a $CO_2$ stripping step where the residual carbamate is removed using a countercurrent fresh $CO_2$ stream.

12 Claims, 4 Drawing Figures

PROCESS FOR UREA PRODUCTION

BACKGROUND OF THE INVENTION

1. Field of the Invention

This invention relates to an improved process for the production of urea from ammonia and carbon dioxide via synthesis at adequate pressure and temperature. The urea formation takes place in a synthesis zone (or zones) where an excess of free ammonia is kept to favour high conversions.

This improved process covers, in particular, a new treatment step to recover and recycle the unreacted materials (free ammonia and carbamate) from the reaction zone (or zones) in an optimal way to minimize energy consumption and investment costs.

2. Description of the Prior Art.

It is known that high reaction yields are favoured by a high ammonia excess (compared with the stoichiometric ratio) which require however a high reactor operating pressure and, as a consequence, complex and energy consuming treatment sections downstream the reactor to remove and recycle said excess ammonia and the residual carbamate from the produced urea.

Some processes have been recently studied to minimize energy and investment requirement for the treatment sections downstream the reactor, but they are still complex and still require considerable amount of energy.

The U.S. Pat. No. 4,208,347 (Montedison), known as the IDR process (Isobaric Double Recycle), describes a two steps stripping treatment scheme where carbamate is removed with ammonia as stripping agent, in the first step, while free ammonia is removed with carbon dioxide as stripping agent, in the second step. A certain complexity of this scheme is evident. The U.S. Pat. No. 4,321,410 (Mitsui Toatsu Chemicals and Toyo Engineering) known as the ACES process (Advanced Process for Cost and Energy Saving) describes a two steps stripping treatment performed in a newly designed stripper where the urea reactor effluent is contacted with the gases (mainly $NH_3$ and $CO_2$) coming from a falling film exchanger in an adiabatic first treatment step where free ammonia is removed and successively treated in the falling film exchanger (second treatment step) counter-currently with carbon dioxide introduced as stripping agent to remove the residual carbamate.

With this process the amount of free ammonia that can be removed from the reactor effluent is limited due to the presence of $NH_3$ in the gases contacting the urea solution in the adiabatic step, while a minimum content of free ammonia in the urea solution is desirable to obtain optimal carbamate removal in the subsequent $CO_2$ stripping step.

The Italian patent application No. 24357A/80 (Snamprogetti) describes a process very similar to the Montedison one but with the two treatment steps at different pressure (non isobaric).

None of the above mentioned new processes achieve the direct recycle to the reactor of the free ammonia separated form the reactor effluent, which is optimal to minimize investment and energy consumption. The indirect recycle of ammonia in the downstream sections is made via acqueous solutions with the recycle of water in the reactor, which is detrimental for reaction yields.

The last generation processes, followed by the cited new generation ones, were dominated by the Stamicarbon $CO_2$ stripping and Snamprogetti $NH_3$ stripping processes both using only one high pressure treatment step. In the Stamicarbon $CO_2$ stripping process, the reactor effluent with a low free ammonia content is directly treated in the $CO_2$ stripper to remove the residual carbamate. The content of ammonia in the reactor is kept low to have optimal carbamate separation in the $CO_2$ stripper, but reaction yields are low with consequent high investment and energy consumption.

In the Snamprogetti $NH_3$ stripping process the reactor effluent with a higher free ammonia content is also directly treated in a "self stripping" treatment step to remove carbamate.

An important amount of free ammonia is still present in the urea solution leaving the stripper and is separately recycled to the reactor using pumps.

This scheme implies the use of a rectifying column to separate pure ammonia with high costs and energy consumption.

None of the last generation processes also achieves the direct recycle to the reactor of the free ammonia separated from the reactor effluents with minimum investment and energy consumption.

SUMMARY OF THE INVENTION

The direct recycle to the reaction zone of important amounts of ammonia is an optimal way of minimizing energy and investment costs which is the main objective of the present invention.

It has been surprisingly discovered that important amounts of ammonia can be economically separated from the effluents of reactors operating with high excess ammonia and therefore with high conversion yields, obtaining minimal excess of ammonia content in the urea solution which can be subsequently treated with maximum efficiency in a falling film exchanger with a counter-current of $CO_2$ stripping stream to remove the residual carbamate.

Knowingly the presence of ammonia is detrimental to $CO_2$ stripping efficiency.

DESCRIPTION OF THE PREFERRED EMBODIMENTS

The new process is described with reference to FIG. 1 which represents one of the possible embodiments of the invention.

The urea solution obtained in the high conversion yield reactor (R) with the presence therefore of a consistant amount of ammonia excess over the stoichiometric amount, is treated in the adiabatic step (S) where the major part of the excess ammonia is removed thanks to the intimate contact of the solution with a small amount of fresh $CO_2$ fed to step (S) by line 1.

Line 2 feeds the urea solution from the reactor (R), which can be of conventional design, to the step (S), while the direct recycle of the separated excess ammonia from step (S) is made through line 3. The urea solution with minimum excess ammonia from step (S) is then fed (line 4) to a $CO_2$ stripper (ST), also of conventional design, where carbamate is removed with maximum efficiency in a falling film exchanger with counter-current fresh $CO_2$ used as stripping agent introduced through line 5.

The vapors (mainly $NH_3$ and $CO_2$ coming from carbamate decomposition) from stripper (ST) are fed through line 6 to the carbamate condenser (CC) where evolved heat is removed producing steam (line 7) utilized for the urea solution conventional treatment steps (not represented in the figure) downstream stripper (ST).

The carbamate condenser (CC) receives also the carbamate solution (line 8) from the above-mentioned, not represented, treatment steps and the inerts introduced with the $CO_2$ which are vented from reactor (R) (line 9). Said inerts, after removal in the carbamate condenser (CC) of the residual $NH_3$ and $CO_2$, are vented from the system (line 20). The feed ammonia (line 10) is partially sent (line 11) to the reactor after preheating, for reactor heat balance purposes, in preheater (P) and partially sent to the carbamate condenser (CC) (line 12). Line 13 feeds the fresh $CO_2$, the major part of which is sent to the stripper (ST) (line 5) and a minor part is sent to step (S) (line 1).

The urea solution (line 14) after treatment in stripper (ST), with optimal residual content of carbamate, is finally sent to the conventional treatment steps to obtain the desired final urea product. The carbamate solution from carbamate condenser (CC) is recycled to reactor by gravity (line 15).

Figure 1:
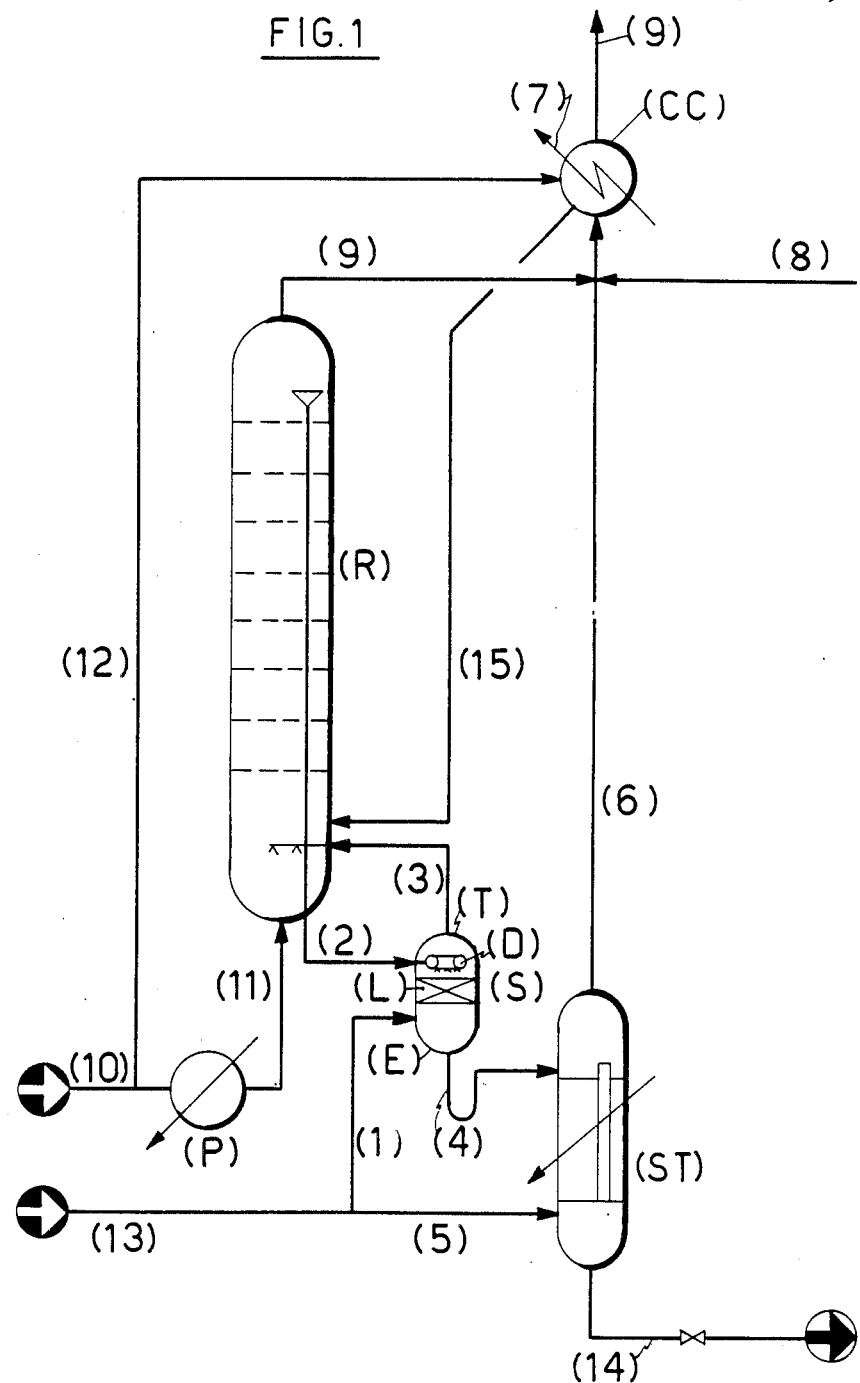
Figure 2:
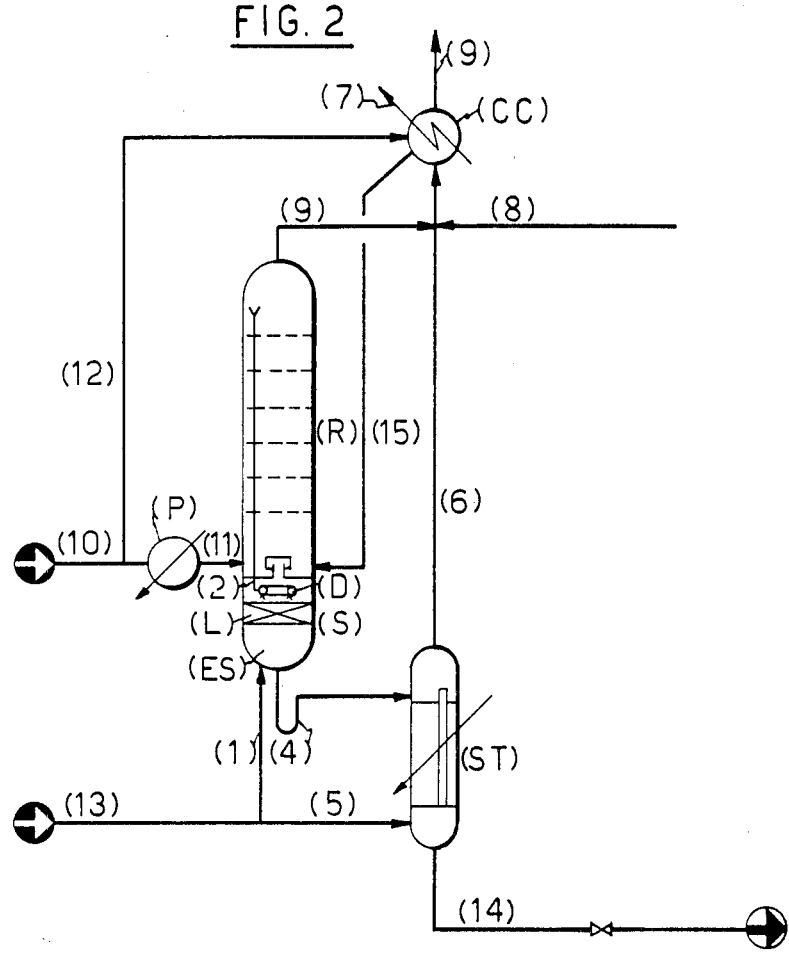
Figure 3:
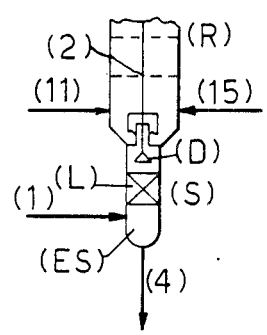

It is critical that an intimate contact of short duration (a few seconds) between the urea solution with excess ammonia and the introduced fresh $CO_2$ be obtained in the adiabatic ammonia separation step (S). FIGS. 1, 2 and 3, where an appropriate layer of mass transfer promoter (L) (for ex. rings or trays) is foreseen, represent different embodiments of the invention, where:

in FIG. 1 the layer of appropriate mass transfer promoter (L) is installed in a separate equipment (E) the top part of which (T) functions as separator for the evolved ammonia collection. An appropriate liquid distributor (D) is also foreseen;

in FIG. 2 the ammonia removal step (S) is located in the bottom part of the reactor (R) where the layer (L) of appropriate mass transfer promoter is installed in a reactor bottom empty space (ES);

in FIG. 3 the ammonia removal step (S) is also located in the bottom part of the reactor (R), where the layer (L) of appropriate mass transfer promoter is installed in a reactor bottom empty space (ES) of reduced diameter.

Figure 4:
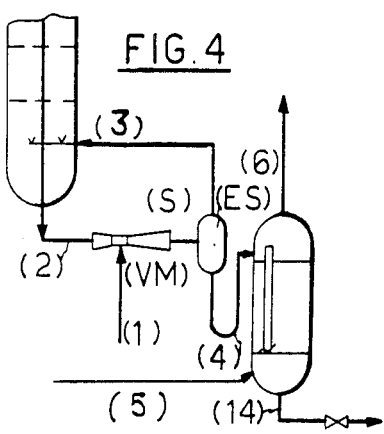

FIG. 4 represents the preferred embodiment of the invention. In the adiabatic ammonia separation step (S) the intimate contact between the urea solution with excess ammonia (stream 2) and the introduced fresh $CO_2$ (stream 1) is obtained in a very short time, achieving a very high mass transfer, in a Venturi type mixer (VM). The evolved ammonia vapor is then separated from the urea solution in the separator (SEP).

The advantageous features of the invention can be evidenced by the following comparison of the energy consumption (steam consumption in the loop) of the above mentioned known processes (last and new generation processes) with those of the examples describing the present invention. The consumption figures of the known processes are taken from Dooyeweerd and Messen, Nitrogen issue n. 143 May 1983.

ACES Process (MT/TEC): 474 kg of 22 bar steam for 1000 kg urea

IDR Process (Montedison): 524 kg of 22 bar steam for 1000 kg urea $CO_2$ Stripping (Stamicarbon): 633 kg of 18 bar steam for 1000 kg urea EXAMPLES 1 and 2: 190 kg of 22 bar steam for 1000 kg urea EXAMPLE 3: 150 kg of 8 bar steam for 1000 kg urea The features of the invention will be better illustrated by the following examples, where isobaric loops are described. The same improved results can be obtained with schemes where the stripper (S) operates at lower pressure than the ammonia separation step (S).

EXAMPLE 1

Reference is made to FIGS. 1, 2, 3 and 4 (isobaric loop)

| Reactor (R) operating conditions | | | |
|---|---|---|---|
| $NH_3/CO_2$ molar ratio | | 4.5 | |
| $H_2O/CO_2$ molar ratio | | 0.4 | |
| temperature | | 188° C. | |
| pressure | | 180 bar | |
| conversion rate ($CO_2$ to urea) | | 74% | |
| Streams composition and quantities | | | |
| Stream (13) Fresh $CO_2$ | | 45.833 kg (100° C.) | |
| Stream (1) Fresh $CO_2$ to the ammonia separation step (S) | | 4.375 kg (100° C.) | |
| Stream (5) Fresh $CO_2$ to the stripper (ST) | | 41.458 kg (100° C.) | |
| Stream (10) Fresh $NH_3$ | | 35.417 kg (25° C.) | |
| Stream (2) Urea solution from reactor | $NH_3$ | 72.250 kg | 40.19% |
| | $CO_2$ | 16.125 kg | 8.97% |
| | Urea | 62.500 kg | 34.77% |
| | $H_2O$ | 28.875 kg | 16.07% |
| | | 179.750 kg | 100.00% |
| | Temperature 188° C. | | |
| Stream (4) Urea solution from the ammonia separation step (S) to the stripper (ST) | $NH_3$ | 29.750 kg | 21.17% |
| | $CO_2$ | 20.000 kg | 14.24% |
| | Urea | 62.500 kg | 44.48% |
| | $H_2O$ | 28.250 kg | 20.11% |
| | | 140.500 kg | 100.00% |
| | Temperature: 191° C. | | |
| Stream (3) Direct recycle of ammonia to the reactor (R) | $NH_3$ | 42.500 kg | 97.42% |
| | $CO_2$ | 500 kg | 1.14% |
| | $H_2O$ | 625 kg | 1.44% |
| | | 43.625 kg | 100.00% |
| | Temperature: 190° C. | | |
| Stream (14) Urea solution from the stripper (ST) | $NH_3$ | 16.000 kg | 12.98% |
| | $CO_2$ | 17.250 kg | 14.00% |
| | Urea | 62.500 kg | 51.71% |
| | $H_2O$ | 27.500 kg | 22.31% |
| | | 123.250 kg | 100.00% |
| | Temperature: 175° C. | | |
| Stream (6) $NH_3$ + $CO_2$ vapors from the stripper (ST) | $NH_3$ | 13.750 kg | 23.43% |
| | $CO_2$ | 44.208 kg | 75.30% |
| | $H_2O$ | 750 kg | 1.27% |
| | | 58.708 kg | 100.00% |
| | Temperature: 190° C. | | |
| Stream (8) Carbamate solution from downstream sections | $NH_3$ | 16.000 kg | 38.10% |
| | $CO_2$ | 17.250 kg | 41.07% |
| | $H_2O$ | 8.750 kg | 20.83% |
| | | 42.000 kg | 100.00% |
| Energy consumption | | | |
| Steam consumption for stripper (ST) | | 190 kg 22 bar steam for 1000 of of urea | |

In the downstream sections (not represented in the figure) for the removal and recycle of the residual $NH_3$ and $CO_2$ contained in the urea solution coming from the $CO_2$ stripper, before final urea solution vacuum concentration to obtain finished product, the 6 to 7 bar steam produced in the carbamate condenser (CC) can be used. By the use of the technique of process to process direct heat recovery (multiple effect system) no extra steam will have to be imported from the plant battery limits.

EXAMPLE 2

Reference is made to FIGS. 1, 2, 3 and 4 (isobaric loop)

| Reactor (R) operating conditions | |
|---|---|
| NH₃/CO₂ Molar Ratio | 4.5 |
| H₂O/CO₂ Molar Ratio | 0.4 |
| temperature | 188° C. |
| pressure | 180 bar |
| conversion rate (CO₂ to urea) | 74% |
| Streams composition and quantities | |

| | | | |
|---|---|---|---|
| Stream (13) Fresh CO₂ | 45.833 kg (100° C.) | | |
| Stream (1) Fresh CO₂ to the ammonia separation step (S) | 1.744 kg (100° C.) | | |
| Stream (5) Fresh CO₂ to the stripper (ST) | 44.084 kg (100° C.) | | |
| Stream (10) Fresh NH₃ | 35.417 kg (25° C.) | | |
| Stream (2) Urea solution from reactor (R) | NH₃ | 72.250 kg | 40.19% |
| | CO₂ | 16.125 kg | 8.97% |
| | Urea | 62.500 kg | 34.77% |
| | H₂O | 28.875 kg | 16.07% |
| | | 179.750 kg | 100.00% |
| | Temperature: 188° C. | | |
| Stream (4) Urea solution from the ammonia separation step (S) to the stripper (ST) | NH₃ | 53.519 kg | 32.96% |
| | CO₂ | 17.669 kg | 10.88% |
| | Urea | 62.500 kg | 38.49% |
| | H₂O | 28.687 kg | 17.67% |
| | | 162.375 kg | 100.00% |
| | Temperature: 191° C. | | |
| Stream (3) Direct recycle of ammonia to the reactor (R) | NH₃ | 18.731 kg | 97.97% |
| | CO₂ | 200 kg | 1.05% |
| | H₂O | 188 kg | 0.98% |
| | | 19.119 kg | 100.00% |
| | Temperature: 190° C. | | |
| Stream (14) Urea solution from the stripper (ST) | NH₃ | 16.000 kg | 12.98% |
| | CO₂ | 17.250 kg | 14.00% |
| | Urea | 62.500 kg | 50.71% |
| | H₂O | 27.500 kg | 22.31% |
| | | 123.250 kg | 100.00% |
| | Temperature: 175° C. | | |
| Stream (6) NH₃ + CO₂ vapors from the stripper (ST) | NH₃ | 37.519 kg | 45.09% |
| | CO₂ | 44.508 kg | 53.49% |
| | H₂O | 1.187 kg | 1.42% |
| | | 83.214 kg | 100.00% |
| | Temperature: 190° C. | | |
| Stream (8) Carbamate solution from downstream sections | NH₃ | 16.000 kg | 38.10% |
| | CO₂ | 17.250 kg | 41.07% |
| | H₂O | 8.750 kg | 20.83% |
| | | 42.000 kg | 100.00% |
| Energy consumption | | | |
| See Example 1. | | | |

EXAMPLE 3

Reference is made to FIGS. 1-2-3 and 4 (isobaric loop). Compared to example 2, operating conditions have been modified to have the stripper (ST) operating in adiabatic conditions. In this case the stripper (ST) could be an apparatus different from a tube exchanger (ex. trays column) but to minimize residence time a falling film type tubes apparatus might still be the best choice as indicated in the figures.

| Reactor (R) operating conditions | |
|---|---|
| NH₃/CO₂ molar ratio | 5 |
| H₂O/CO₂ molar ratio | 0.5 |
| Temperature | 190° C. |
| Pressure | 200 bar |
| Conversion rate (CO₂ to urea) | 76% |
| Streams composition and quantities | |

| | | | |
|---|---|---|---|
| Stream (13) Fresh CO₂ | 45.833 kg (100° C.) | | |
| Stream (1) Fresh CO₂ to the ammonia separation step (S) | 4.875 kg (100° C.) | | |
| Stream (5) Fresh CO₂ to the stripper (ST) | 40.958 kg (100° C.) | | |
| Stream (10) Fresh NH₃ | 35.417 kg (25° C.) | | |
| Stream (2) Urea solution from reactor | NH₃ | 81.062 kg | 42.86% |
| | CO₂ | 14.500 kg | 7.67% |
| | Urea | 62.500 kg | 33.05% |
| | H₂O | 31.063 kg | 16.42% |
| | | 189.125 kg | 100.00% |
| | Temperature 190° C. | | |
| Stream (4) Urea solution from the ammonia separation step (S) to the stripper (ST) | NH₃ | 29.750 kg | 21.03% |
| | CO₂ | 18.875 kg | 13.35% |
| | Urea | 62.500 kg | 44.19% |
| | H₂O | 30.313 kg | 21.43% |
| | | 141.438 kg | 100.00% |
| | Temperature 192° C. | | |
| Stream (3) Direct recycle of ammonia to the reactor (R) | NH₃ | 51.312 kg | 97.62% |
| | CO₂ | 500 kg | 0.95% |
| | H₂O | 750 kg | 1.43% |
| | | 52.562 kg | 100.00% |
| | Temperature 191° C. | | |
| Stream (14) Urea solution from the stripper (ST) | NH₃ | 20.625 kg | 15.24% |
| | CO₂ | 22.500 kg | 16.63% |
| | Urea | 62.500 kg | 46.19% |
| | H₂O | 29.688 kg | 21.94% |
| | | 135.313 kg | 100.00% |
| | Temperature 165° C. | | |
| Stream (6) NH₃ + CO₂ vapors from the stripper (ST) | NH₃ | 9.125 kg | 19.38% |
| | CO₂ | 37.333 kg | 79.29% |
| | H₂O | 625 kg | 1.33% |
| | | 47.083 kg | 100.00% |
| | Temperature 192° C. | | |
| Energy consumption | | | |
| Steam consumption for stripper (ST): zero | | | |

In the downstream sections (not represented in the figure), for the removal and recycle of the higher residual NH₃ and CO₂ contained in the urea solution coming from the CO₂ stripper, before final urea solution vacuum concentration to obtain finished product, the 7 to 8 bar steam produced in the carbamate condenser (CC) can be used.

By the use of the technique of process to process direct heat recovery (multiple effect system), a reduced amount of 150 kg for 1000 kg urea of 8 bar steam will have to be imported from the plant battery limits.

EXAMPLE 4

This example refers to the last generation Stamicarbon CO₂ stripping process modified according to the invention (see FIGS. 1, 2, 3 and 4) in a case of a Stamicarbon CO₂ stripping plant modernization to reduce energy consumption.

| Reactor (R) operating conditions | |
|---|---|
| NH₃/CO₂ molar ratio | 3.2 |
| H₂O/CO₂ molar ratio | 0.4 |
| Temperature | 184° C. |
| Pressure | 145 bar |
| Conversion rate (CO₂ to urea) | 62% |
| Streams composition and quantities | |

| | | | |
|---|---|---|---|
| Stream (13) Fresh CO₂ | 45.833 kg (100° C.) | | |
| Stream (1) Fresh CO₂ to the ammonia separation step (S) | 2.112 kg (100° C.) | | |
| Stream (5) Fresh CO₂ to the stripper (ST) | 43.721 kg (100° C.) | | |
| Stream (10) Fresh NH₃ | 35.417 kg (25° C.) | | |
| Stream (2) Urea solution from reactor | NH₃ | 56.000 kg | 31.55% |
| | CO₂ | 28.125 kg | 15.84% |
| | Urea | 62.500 kg | 35.21% |
| | H₂O | 30.875 kg | 17.40% |
| | | 177.500 kg | 100.00% |
| | Temperature 184° C. | | |
| Stream (4) Urea solution from the ammonia separation step (S) to the stripper (ST) | NH₃ | 44.250 kg | 26.44% |
| | CO₂ | 30.037 kg | 17.95% |
| | Urea | 62.500 kg | 37.34% |
| | H₂O | 30.575 kg | 18.27% |
| | | 167.362 kg | 100.00% |
| | Temperature 185° C. | | |
| Stream (5) Direct recycle of | NH₃ | 11.750 kg | 95.92% |

-continued

| | | | |
|---|---|---|---|
| ammonia to the reactor (R) | $CO_2$ | 200 kg | 1.63% |
| | $H_2O$ | 300 kg | 2.45% |
| | | 12.250 kg | 100.00% |
| | Temperature 185° C. | | |
| Stream (14) Urea solution from the stripper (ST) | $NH_3$ | 9.133 kg | 8.22% |
| | $CO_2$ | 10.846 kg | 9.77% |
| | Urea | 62.500 kg | 56.28% |
| | $H_2O$ | 28.575 kg | 25.73% |
| | | 111.054 kg | 100.00% |
| | Temperature 170° C. | | |
| Stream (6) $NH_3$ + $CO_2$ vapors from the stripper (ST) | $NH_3$ | 35.117 kg | 35.10% |
| | $CO_2$ | 62.919 kg | 62.90% |
| | $H_2O$ | 2.000 kg | 2.00% |
| | | 100.036 kg | 100.00% |
| | Temperature 185° C. | | |
| Stream (8) Carbamate solution from downstream sections | $NH_3$ | 9.133 kg | 30.64% |
| | $CO_2$ | 10.846 kg | 36.39% |
| | $H_2O$ | 9.825 kg | 32.97% |
| | | 29.804 kg | 100.00% |

Energy Consumption

The 22 bar steam consumption in the loop ($CO_2$ stripper) is reduced of 100 kg for 1000 kg urea with a modest investment for the installation of the ammonia separation step (S).

EXAMPLE 5

This example refers to the use of the invention for the revamping of the total or partial recycle conventional non stripping processes (Montedison, Mitsui Toatsu, etc), to reduce energy consumption. With the use of the ammonia separation and direct ammonia recycle step (S), to treat the urea solution from the reactor, before the first decomposition step, a smaller quantity of ammonia and, as a consequence, of water, will have to be recycled in the downstream sections, improving reactor conversion yields with the reduction of water vaporization. For both the above mentioned reasons (higher conversion yields and, consequently, less carbamate to be recycled and less vaporised water) a reduction of the 8 to 15 bar battery limits steam, of 300 kg per 1000 kg urea can be obtained.

EXAMPLE 6

This example refers to the use of the invention for the revamping of the Snamprogetti $NH_3$ stripping plants, to reduce energy consumption and maintenance and operating costs.

With the use of the ammonia separation and recycle step (S), in this case located downstream the stripper, to remove the high excess ammonia content in the treated urea solution stream (the high excess ammonia of the urea solution from the reactor favours the $NH_3$ self-stripping carbamate separation in the stripper), a smaller quantity of ammonia will have to be recycled in the downstream sections. The use of the rectifying column to separate and recycle pure ammonia with high costs and energy consumption, is so avoided.

I claim:

1. In a process for the production of urea from ammonia and carbon dioxide at an effective pressure and temperature, wherein the urea formation takes place in at least one synthesis zone and in which an excess of free ammonia is present to favor high conversions, thereby producing a urea composition containing an excess of free ammonia, residual carbamate and urea and the residual carbamate is removed by stripping the urea composition with a counter current stream of a major amount of fresh $CO_2$, the improvement comprising prior to contacting the urea composition with the major amount of fresh $CO_2$, adiabatically contacting the urea composition with a minor amount of fresh $CO_2$ to thereby remove an amount of $NH_3$ from the urea composition which is substantially free of water vapor and directly recycling the $NH_3$ to the synthesis zone.

2. In a process for the production of urea from ammonia and carbon dioxide at an effective pressure and temperature, wherein the urea formation takes place in at least one synthesis zone and in which an excess of free ammonia is present to favor high conversions, thereby producing a urea composition containing an excess of free ammonia, residual carbamate and urea and the residual carbamate is removed by stripping the urea composition with a counter current stream of a major amount of fresh $CO_2$, the improvement comprising prior to contacting the urea composition with the major amount of fresh $CO_2$, adiabatically contacting the urea composition with a minor amount of fresh $CO_2$ to thereby remove an amount of $NH_3$ from the urea composition which is substantially free of water vapor.

3. The process of claim 1 or 2, wherein the adiabatic contacting step is performed in a Venturi mixer and the fresh $CO_2$ flows co-currently with the urea composition.

4. The process of claim 1 and 2 wherein the adiabatic contacting step is performed using a layer of an effective mass transfer promoter and the fresh $CO_2$ flows counter-currently to the urea composition.

5. The process of claims 1 or 2 wherein the duration of contacting between the urea composition and the minor amount of fresh $CO_2$ is less than about 10 seconds.

6. The process of claim 1 or 2, wherein the minor amount of $CO_2$ is from about 4 to 12% by weight of total $CO_2$.

7. The process of claim 1 or 2, wherein the minor amount of $CO_2$ is less than about 20% by weight of total $CO_2$.

8. The process of claim 1 or 2, wherein the stripping step operates in an adiabatic condition whereby any heat required for residual carbamate removal is supplied by a reduction heat produced by part of the major amount of fresh $CO_2$ reacting with free ammonia to form carbamate.

9. The process of claim 1 or 2, wherein the synthesis zone operates at a pressure in the range of 120 to 250 kg/cm$^2$.

10. The process of claim 1 or 2, wherein the $NH_3$/$CO_2$ molar ratio in the synthesis zone is in the range of 2.5 to 6.

11. The process of claim 1 or 2, wherein the stripping step operates at a lower pressure than the adiabatic contacting step.

12. The process of claim 8, wherein the stripping step for removing residual carbamate is uses a falling film exchanger.

* * * * *